United States Patent
Schader et al.

(10) Patent No.: US 10,874,800 B2
(45) Date of Patent: Dec. 29, 2020

(54) MEDICAMENT INJECTION DEVICE

(71) Applicant: SANOFI-AVENTIS DEUTSCHLAND GMBH, Frankfurt am Main (DE)

(72) Inventors: Marc Schader, Frankfurt am Main (DE); Michael Helmer, Frankfurt am Main (DE); Sebastian Braun, Dresden (DE); Michael Varga, Donzdorf (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 117 days.

(21) Appl. No.: 15/778,129

(22) PCT Filed: Nov. 21, 2016

(86) PCT No.: PCT/EP2016/078265
§ 371 (c)(1),
(2) Date: May 22, 2018

(87) PCT Pub. No.: WO2017/089276
PCT Pub. Date: Jun. 1, 2017

(65) Prior Publication Data
US 2018/0326155 A1    Nov. 15, 2018

(30) Foreign Application Priority Data
Nov. 27, 2015  (EP) ...................... 15196696

(51) Int. Cl.
*A61M 5/24* (2006.01)
*A61M 5/32* (2006.01)

(52) U.S. Cl.
CPC ............ *A61M 5/2466* (2013.01); *A61M 5/24* (2013.01); *A61M 5/2455* (2013.01);
(Continued)

(58) Field of Classification Search
CPC .... A61M 5/32; A61M 5/2455; A61M 5/2466; A61M 5/3204; A61M 5/3293;
(Continued)

(56) References Cited

U.S. PATENT DOCUMENTS 4,850,996 A * 7/1989 Cree ..................... A61M 5/326
                                                      604/198
7,828,778 B2 * 11/2010 Liversidge .......... A61M 5/3205
                                                      604/198
(Continued)

FOREIGN PATENT DOCUMENTS

CN         102821802        12/2012
WO     WO 2011/095488      8/2011

OTHER PUBLICATIONS

International Search Report and Written Opinion in International Application No. PCT/EP2016/078265, dated Feb. 28, 2017, 9 pages.
(Continued)

*Primary Examiner* — Quynh-Nhu H. Vu
(74) *Attorney, Agent, or Firm* — Fish & Richardson P.C.

(57) ABSTRACT

A medicament injection device is provided. The device includes a main body configured to receive a medicament cartridge sealed with a penetrable holder. The device can further include a needle holder holding a needle, a needle sleeve arranged to be axially movable with respect to the main body, and a retainer coupled to the needle holder and to the needle sleeve. The retainer can be axially movable with respect to the main body along the main axis of the device. Upon displacement of the needle sleeve and the retainer by a predefined distance towards a proximal end of the main body, the needle holder and the needle can be displaced axially towards the proximal end of the main body and decouple from the retainer. The needle sleeve can be
(Continued)

configured to disengage from the needle holder upon displacement of the needle sleeve.

12 Claims, 4 Drawing Sheets

(52) U.S. Cl.
CPC ........ *A61M 5/3204* (2013.01); *A61M 5/3293* (2013.01); *A61M 2005/2474* (2013.01)

(58) Field of Classification Search
CPC ........ A61M 5/20; A61M 5/2429; A61M 5/34; A61M 5/344; A61M 5/346; A61M 5/348; A61M 5/284; A61M 5/28; A61M 5/2448; A61M 2005/2474; A61M 2005/2013; A61M 2005/206; A61M 2005/208; A61M 2005/2488; A61M 2005/2485; A61M 2005/247; A61M 2005/2451; A61M 2005/2403; A61M 2005/2407; A61M 5/24
See application file for complete search history.

(56) References Cited

U.S. PATENT DOCUMENTS

| | | | |
|---|---|---|---|
| 8,647,306 B2* | 2/2014 | Schwirtz | A61M 5/002 604/192 |
| 9,072,841 B2* | 7/2015 | Thueer | A61M 5/326 |
| 9,155,838 B2* | 10/2015 | Bilton | A61M 5/2448 |
| 9,987,436 B2* | 6/2018 | Giambattista | A61M 5/3146 |
| 10,518,032 B2* | 12/2019 | Helmer | A61M 5/2466 |
| 10,610,645 B2* | 4/2020 | Helmer | A61M 5/24 |
| 2003/0144633 A1 | 7/2003 | Kirchhofer | |
| 2006/0030819 A1 | 2/2006 | Young et al. | |
| 2011/0276008 A1* | 11/2011 | Matthias | A61M 5/34 604/201 |
| 2012/0283646 A1* | 11/2012 | Kouyoumjian | A61M 5/2466 604/192 |

OTHER PUBLICATIONS

International Preliminary Report on Patentability in International Application No. PCT/EP2016/078265, dated May 29, 2018, 7 pages.

* cited by examiner

MEDICAMENT INJECTION DEVICE

CROSS-REFERENCE TO RELATED APPLICATIONS

The present application is the national stage entry of International Patent Application No. PCT/EP2016/078265, filed on Nov. 21, 2016, and claims priority to Application No. EP 15196696.7, filed on Nov. 27, 2015 the disclosures of which are incorporated herein by reference.

TECHNICAL FIELD

The present disclosure relates to a medicament delivery device.

BACKGROUND

Medicament injection devices can take various forms. One form uses a syringe, where medicament is stored in a hollow cylinder, typically formed of glass. The medicament is sealed from the environment with a plunger moveable within the cylinder, and a needle fluidly connected to the syringe's distal end. The needle must remain capped in order to maintain the medicament under sterile conditions.

Another form of injection device uses a cartridge instead of a syringe, the cartridge having a distal seal instead of the syringe's needle. Typically a patient connects a double-ended needle to the cartridge before injection, thereby piercing the cartridge's seal with the proximal tip of the double-ended needle.

While a cartridge can provide handling and storage advantages relative to syringes, they are not without shortcomings. For example, the attachment of a needle to the cartridge requires an additional step. This step can be problematic for patients with limited dexterity, poor coordination, or who have lost a degree of sensation in their hands. Even with such disadvantages, in certain situations it is desirable to provide an injection device in which the needle is kept separate from the medicament until such time as the patient wishes to commence the injection. The injection device described herein aims to overcome one or more problems associated with prior devices.

SUMMARY

A first embodiment provides a medicament injection device comprising a main body configured to receive a medicament cartridge sealed with a penetrable barrier, a needle holder holding a needle, a needle sleeve arranged around at least a portion of the needle holder and needle, and arranged to be axially movable with respect to the main body; and a retainer coupled to the needle holder and to the needle sleeve and axially movable with respect to the main body along the main axis of the device; wherein the retainer is coupled to the needle holder so that, upon displacement of the needle sleeve and the retainer by a predefined distance towards a proximal end of the main body, the needle holder and needle are displaced axially towards the proximal end of the main body and decouple from the retainer; and wherein the needle sleeve is configured to disengage from the needle holder upon axial displacement of the needle sleeve in the proximal direction beyond the predefined distance.

The needle holder may be configured to dock with a medicament cartridge received by the main body.

In a first position, the needle sleeve may be coupled to the retainer so that axial movement of the needle sleeve in a proximal direction causes the axial displacement of the retainer, the needle carrier and the needle in a proximal direction.

The needle holder may comprise a female part arranged to dock with a medicament cartridge having a male part to form a frictional fit with respect to each other subsequent to displacement of the needle holder by the predefined distance.

The needle holder further may comprise a lip configured to prevent subsequent axial displacement of the needle holder and needle with respect to the medicament cartridge subsequent to the needle holder docking with the medicament cartridge.

The main body may comprise a slotted ramp and the retainer may comprise one or more radial members, wherein axial movement of the one or more radial members over the slotted ramp causes outward radial movement of the radial members, thereby causing the retainer to disengage from the needle holder.

The needle holder may comprise a flexible lever configured to flex and disengage from the retainer in response to the retainer moving axially by the predefined distance in the proximal direction.

The retainer may comprise one or more radial members each configured to separate into two parts subsequent to axial displacement by the predefined distance.

The device may contain a medicament cartridge and wherein the needle penetrates the barrier of the medicament cartridge upon displacement of the needle holder displacement member by a predefined distance in the proximal direction.

The device may contain a medicament cartridge containing a medicament.

The device may be an auto-injector device.

A second embodiment provides a method of operating a medicament injection device, the method comprising: pushing a retainer in a proximal axial direction, thereby causing the needle holder and needle to be displaced axially towards the proximal end of the main body and to decouple from the retainer.

BRIEF DESCRIPTION OF THE DRAWINGS

Exemplary embodiments of the present disclosure are described with reference to the accompanying drawings, in which.

DETAILED DESCRIPTION

Embodiments of the current disclosure provide a mechanism for inserting a needle of an injection device into a cartridge containing a medicament for injection by a patient or care giver. The mechanism allows the medicament cartridge to remain sealed until such time as the user wishes to commence the injection. Automating a mechanism for inserting the needle into the medicament cartridge also reduces the amount of handling of the needle by the user prior to the injection. Indeed, in some embodiments described below, the user does not touch the needle when the needle is inserted into the medicament cartridge.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1:
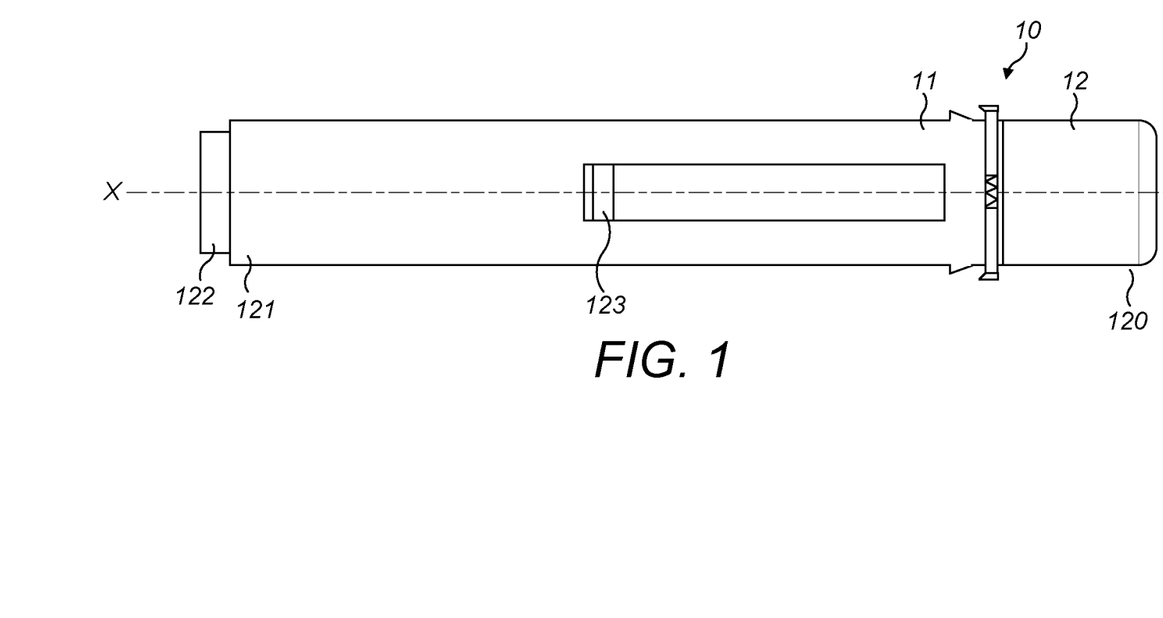
FIG. 1 is a side-on view of an auto-injector device according to an embodiment of the disclosure.

According to some embodiments of the present disclosure, an exemplary drug delivery device 10 is shown in FIG. 1. Device 10, as described above, is configured to inject a medicament into a patient's body. Device 10 includes a main body 11 which typically contains a reservoir containing the medicament to be injected (e.g., a syringe) and the components required to facilitate one or more steps of the delivery process. Device 10 can also include a cap assembly 12 that can be detachably mounted to the main body 11. In some implementations, a user may be required to remove cap 12 from main body 11 before device 10 can be operated.

As shown, main body 11 is substantially cylindrical and has a substantially constant diameter along the longitudinal axis X. The main body 11 has a distal region 120 and a proximal region 121. The term "distal" refers to a location that is relatively closer to a site of injection, and the term "proximal" refers to a location that is relatively further away from the injection site.

Device 10 can also include a needle sleeve 24 (see FIGS. 2-7) coupled to main body 11 to permit movement of sleeve 24 relative to main body 11. For example, sleeve 24 can move in a longitudinal direction parallel to longitudinal axis X. Specifically, movement of sleeve 24 in a proximal direction can permit a needle 17 to extend from distal region 120 of main body 11.

Insertion of needle 17 can occur via several mechanisms. For example, needle 17 may be fixedly located relative to main body 11 and initially be located within an extended needle sleeve 24. Proximal movement of sleeve 24 by placing a distal end of sleeve 24 against a patient's body and moving main body 11 in a distal direction will uncover the distal end of needle 17. Such relative movement allows the distal end of needle 17 to extend into the patient's body. Such insertion is termed "manual" insertion as needle 17 is manually inserted via the patient's manual movement of main body 11 relative to sleeve 24.

Another form of insertion is "automated," whereby needle 17 moves relative to main body 11. Such insertion can be triggered by movement of sleeve 24 or by another form of activation, such as, for example, a button 122. As shown in FIG. 1, button 122 is located at a proximal end of main body 11. However, in other embodiments, button 122 could be located on a side of main body 11.

Other manual or automated features can include drug injection or needle retraction, or both. Injection is the process by which a bung or piston 123 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 121 of main body 11, and a distal end of the drive spring can be configured to apply a compressive force to a proximal surface of piston 123. Following activation, at least part of the energy stored in the drive spring can be applied to the proximal surface of piston 123. This compressive force can act on piston 123 to move it in a distal direction. Such distal movement acts to compress the liquid medicament within the syringe, forcing it out of needle 17.

Following injection, needle 17 can be retracted within sleeve 24 or main body 11. Retraction can occur when sleeve 24 moves distally as a user removes device 10 from a patient's body. This can occur as needle 17 remains fixedly located relative to main body 11. Once a distal end of sleeve 24 has moved past a distal end of needle 17, and needle 17 is covered, sleeve 24 can be locked. Such locking can include locking any proximal movement of sleeve 24 relative to main body 11.

Another form of needle retraction can occur if needle 17 is moved relative to main body 11. Such movement can occur if the syringe within main body 11 is moved in a proximal direction relative to main body 11. This proximal movement can be achieved by using a retraction spring (not shown), located in distal region. A compressed retraction spring, when activated, can supply sufficient force to the syringe to move it in a proximal direction. Following sufficient retraction, any relative movement between needle 17 and main body 11 can be locked with a locking mechanism. In addition, button 122 or other components of device 10 can be locked as required.

Figure 2A:
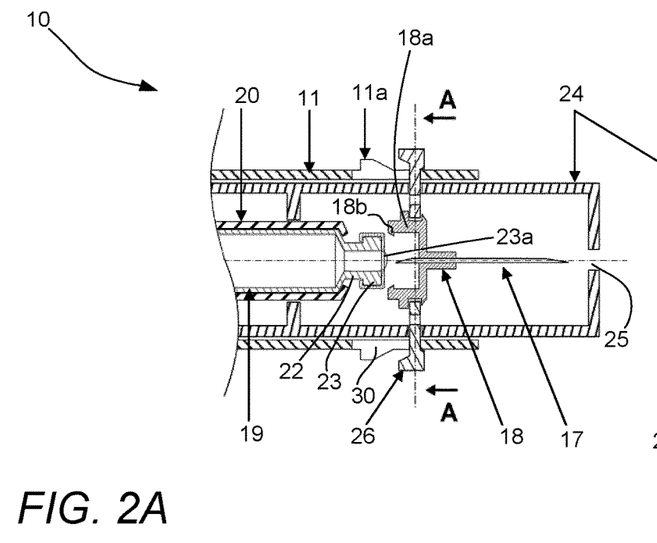
FIG. 2A is a side-on cross sectional schematic view of the device shown in FIG. 1.

FIG. 2A shows a side-on cross-section of an auto-injector device 10 according to a first embodiment of the disclosure.

The auto-injector device 10 comprises a cartridge 19 which is held in place by a cartridge holder 20. The cartridge holder 20 and cartridge 19 are connected and fixed relative to the main body 11 of the device 10. The cartridge 19 has a cartridge body 21 a neck 22 and a head 23. The head 23 is wider than the neck 22, thereby forming a flanged end. The neck 22 and head 23 contain a passage allowing medicament to pass therethrough as well as to receive the needle 17 once inserted. The head 23 is provided with a penetrable barrier such as a septum 23a to close off the passage and to seal the contents of the medicament cartridge 19. The cartridge body 21, neck 22 and head 23 may be generally cylindrical in shape. However, alternative shapes may be employed.

The needle holder 18 which holds the needle 17 is axially movable relative to the main body 11 and the cartridge 19. The needle holder has a generally cup-shaped portion 18a and a passage through which the needle 17 passes. The cup-shaped portion 18a is shaped to engage with the head 23 of the cartridge 19. The cup-shaped portion 18a comprises a lip 18b which serves to clip onto the head 23 to prevent detachment of the needle holder 18 from the cartridge 19 subsequent to attachment of the needle holder 18 to the cartridge 19.

The device 10 comprises a tubular needle sleeve 24. The needle sleeve 24 is a protective sleeve that prevents unwanted exposure of the needle 17. The needle sleeve has a generally similar shape to the main body and is hollow and generally cylindrical. The needle sleeve 24 fits inside the main body 11. The needle sleeve 24 is arranged so that it can slide axially relative to the main body 11. The needle sleeve 24 has an aperture 25 at the distal end thereof to allow the needle to contact the patient's skin.

Figure 2B:
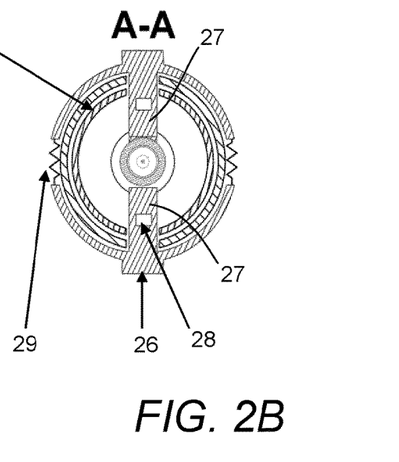
FIG. 2B is cross-section taken through the line A-A in FIG. 2A.

The device 10 comprises a retainer 26 which is annular or tubular in shape. As shown in FIG. 2B, the retainer 26 has a generally circular cross-section. The retainer 26 has first and second radial members 27 which extend from the curved wall of the retainer 26 inwardly to engage with the needle holder 18. Each of the radial members 27 is provided with a hole 28 which, as explained below, is arranged to receive the needle sleeve 24 as the retainer 26 is moved axially towards the cartridge 19. The curved wall of the retainer 26 is provided with one or more expansion elements 29. The expansion elements 29 are configured to enlarge the cross-sectional circumference of the retainer 26 as the retainer 26 moves over the ramped portion of the main body 11.

As shown in FIG. 2A, each of the radial members 27 extend through apertures located in the wall of the needle sleeve 24 and through elongate slits 30 in the wall of the main body 11. The ends of the radial members 27 extending through the slits 30 are flanged so that the flanges sit on the outer surface of the main body 11.

The main body 11 comprises a slotted ramp 11a around each of the slits 30. The ramp 11a is arranged so that the outer diameter of the wall of the main body 11 (from one slit 30 to the second slit 30 shown in FIGS. 2B and 3B) is greater at the end of the slits 30 proximate the head 23 of the medicament cartridge 19 than it is at end of the slits 30 located away from the head 23 of the medicament cartridge 19 and towards the distal end of the device 10. As explained in more detail below, the ramp configuration causes the retainer 26 to expand as it moves axially towards the medicament cartridge 19, eventually leading to the radial members 27 decoupling from the needle holder 18 once the retainer 26 moves axially beyond a predefined distance towards the medicament cartridge 19.

FIGS. 2A and 2B show the components of the device 10 in their initial position prior to insertion of the needle into the medicament cartridge in preparation for the injection of medicament into the patient.

Figure 3A:
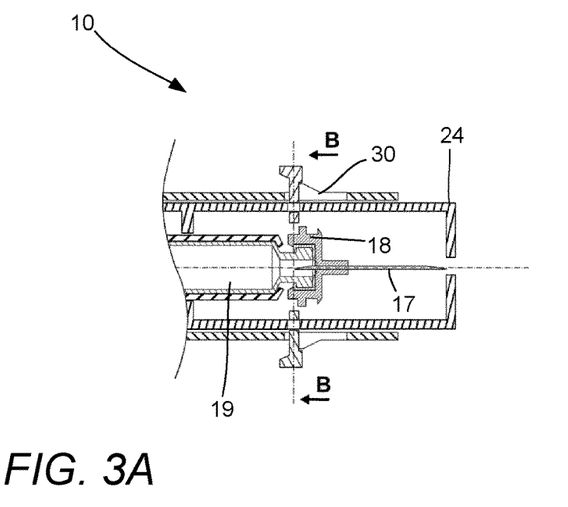
FIG. 3A is a side-on cross sectional schematic view of the device during a stage of use.

FIG. 3A shows a side-on cross-section of the auto-injector device 10 as the user pushes the needle sleeve 24 in the direction of the bold arrows up to the predefined distance d at which point the retainer 26 decouples from the needle holder 18.

The needle sleeve 24 is coaxial with respect to main body 11 and slides along inside the main body 11 of the device 10. The axial movement of the sleeve 24 causes the retainer 26 to move axially towards the medicament cartridge 19 since the radial members 27 abut the needle sleeve and are fixed relative to the needle sleeve 24. Each of the radial members 27 abuts at one end thereof to the needle holder 18. The axial movement of the radial members 27 thereby causes the needle holder 18 and the needle 17 to move axially towards the medicament cartridge 19.

After moving axially by a predefined distance, the cup-shaped part 18a of the needle holder 18 fits over the head 23 of the medicament cartridge 19. The lip 18b extending around the cup-shaped part 18a of the needle holder serves to fix the needle holder 18 to the medicament cartridge 19. The lip 18b has a tapered leading edge to allow the cup shaped part to fit over the head 23. However, once the needle holder 18 is fitted to the medicament cartridge 19, axial movement of the needle holder away, and separation from, the medicament cartridge 19 is prevented by the lip.

Alternatively, the diameter of the cup shaped part 18a and the diameter of the head 23 of the medicament cartridge 19 may be arranged to ensure a close frictional fit between the needle holder 18 and the medicament cartridge 19. In embodiments having a close frictional fit, no lip may be provided.

As shown in FIG. 3, the needle 17 pierces the septum 23*a* of the medicament cartridge 19, thereby establishing a passage for the medicament to flow from the medicament cartridge 19 to the distal end of the needle 17. Both ends of the needle 17 are sharp. The proximal end is sufficiently sharp to enable the needle 17 to penetrate the septum 23*a* of the medicament cartridge 19. The distal end of the needle 17 is sufficiently sharp to allow the needle to penetrate the patient's skin.

During axial movement towards the medicament cartridge 19, the radial members 27 are guided along the respective slits 30 located in the wall of the main body 11. Since the part of the wall of the main body 11 containing the slits is ramped, the flanged ends of the radial members 27 extending through the slits 30 causes a radial displacement of each of the radial members 27. As such, the retainer 26 decouples from the needle holder 18 at the point shown in FIG. 3. The holes 28 in the radial members 27 align radially with the needle sleeve 24. The needle sleeve 24 is provided with longitudinal slits (not shown) to allow the needle sleeve 24 to slide through the radial members 27 as the needle sleeve 24 is displaced axially subsequent to attachment of the needle holder 18 to the medicament cartridge 19, as shown in FIG. 4.

The decoupling of the retainer 26 from the needle holder 18 and the docking of the needle holder 18 with the medicament cartridge 19 may provide audible feedback, such as a clicking sound, informing the user that the needle has been inserted into the medicament cartridge 19. Once the needle 17 has been inserted in to the medicament cartridge 19 and the needle holder 18 attached thereto, the device is ready to commence injection of the medicament. The distal end of the device 10 may then be placed against the injection site located on the patient's skin.

Figure 4:
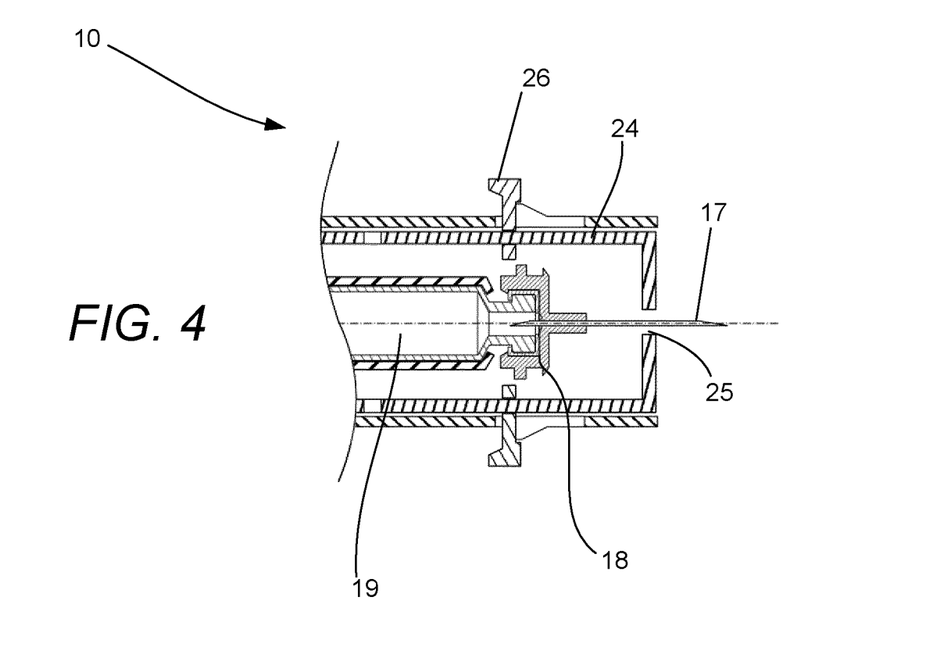
FIG. 4 is a side-on cross sectional schematic view of the device during a stage of use subsequent to the stage shown in FIG. 3.

FIG. 4 shows a side-on cross-section of the auto-injector device 10 as the needle sleeve 24 moves, relative to the main body 11, in the direction of the bold arrows beyond the predefined distance at which point the needle sleeve 24 decouples from the needle holder 18.

This relative movement can be caused by a user gripping the main body 11 and pushing the needle sleeve 24 towards the proximal end of the device 10. Alternatively, the distal end of the needle sleeve 24 may be held against the patient's skin at the injection site. As the user pushes the device 10 against the injection site, the outer wall of the main body 11 slides over the needle sleeve 24 thereby causing the needle sleeve 24 to retract relative to the main body 11.

After the radial members 27 have each separated from the needle holder 18, axial movement of the needle sleeve 24 towards the proximal end of the device 10 is no longer coupled to corresponding movement of the needle holder 18. In other words, once the needle sleeve 24 is pushed beyond the predefined distance, the needle sleeve 24 disengages from the needle holder 18 which remains fixed to the medicament cartridge 19.

Since the needle 17 and needle holder 18 are no longer coupled to the needle sleeve 24 and are instead fixed with respect to the medicament cartridge 19 and the main body 11, this further axial movement of the needle sleeve 24 causes the needle 17 to emerge from the aperture 25 in the distal end of the needle sleeve 24. If the device 10 has been placed against the injection site the needle 17 pierces the patient's skin.

Figure 3B:
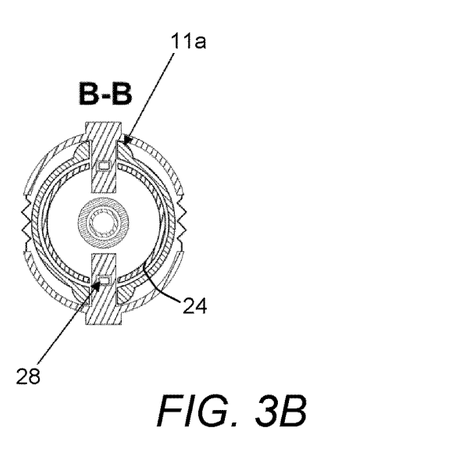
FIG. 3B is cross-section taken through the line B-B in FIG. 3A.

While the axial movement of the needle holder 18 may be caused by the user pushing the needle sleeve 24 thereby pushing the retainer 26, as shown in FIGS. 2 and 3, it is also possible for the user to push the retainer 26 directly, thereby causing the needle sleeve 24 and needle holder 18 to move axially towards the proximal end of the device 10. The ends of the radial members 27 extending through the slits 30 may have an enlarged surface to allow the user to push the radial members 27 directly.

In the embodiment shown in FIGS. 1-4, the retainer 26 is provided with two radial members 27. However, in alternative embodiments, more members may be provided.

Figure 5:
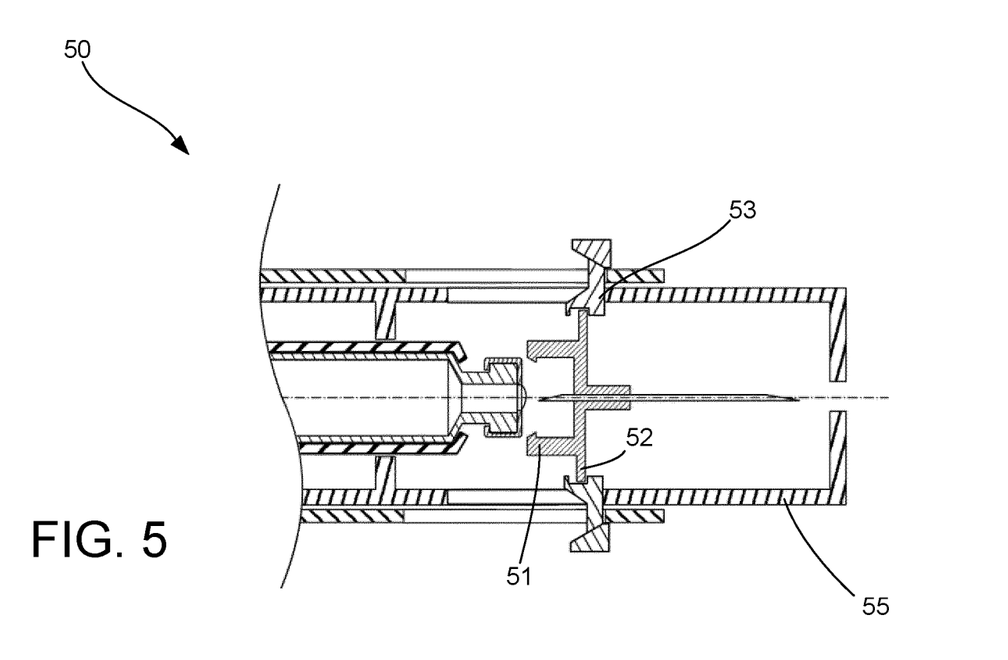
FIG. 5 is a side-on cross sectional schematic view of a device according to an alternative embodiment.
Figure 6:
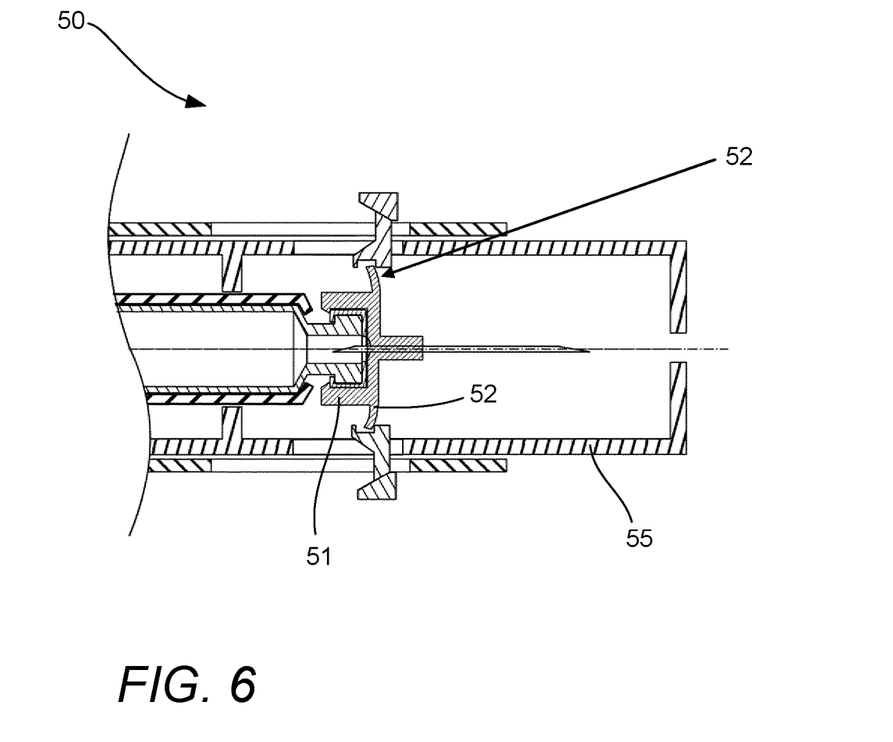
FIG. 6 is a side-on cross sectional schematic view of the device shown in FIG. 5 as a needle holder is attached to a medicament cartridge.
Figure 7:
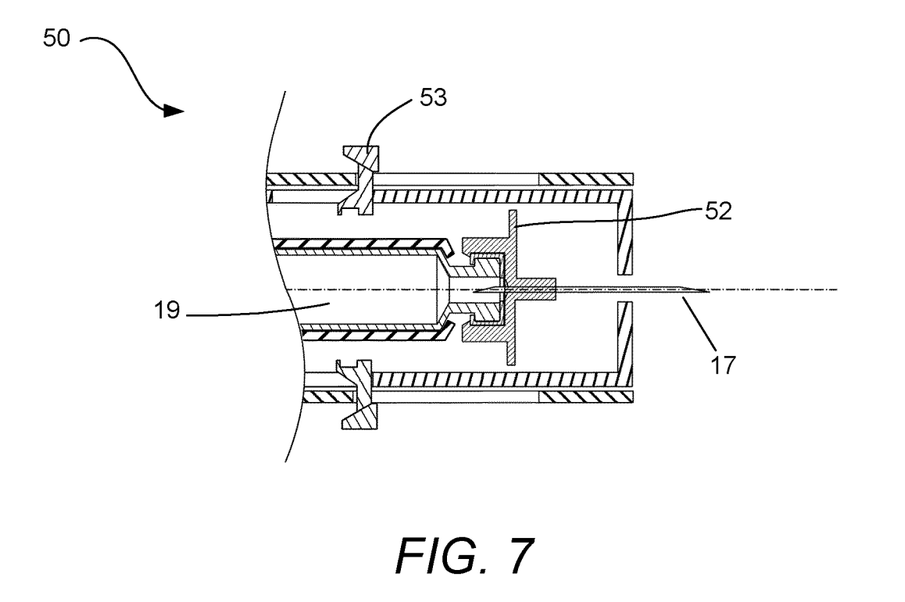
FIG. 7 is a side-on cross sectional schematic view of the device shown in FIGS. 5 and 6 showing subsequent movement of the needle sleeve.

An alternative embodiment of the disclosure, which is a variation of the embodiments described above with reference to FIGS. 2-4, is shown in FIGS. 5-7.

A device 50 may be provided having an overall structure similar to the device 10 described above. Aspects of the device 50 that are substantially the same as aspects described above with respect to the device 10 will not be repeated.

The device 50 has a needle holder 51 which is similar to the needle holder 18 except that the needle holder 51 has one or more bending elements or levers 52 that are arranged to engage with a retainer 53. The main body 54 and the needle sleeve 55 are both provided with apertures through which the retainer 53 extends.

As either the retainer 53 or needle sleeve 55 is pushed axially in a similar manner to that described above the needle holder 51 is pushed axially in a proximal direction towards the medicament cartridge 19. As above, the needle holder 51 becomes fixed to the medicament cartridge 19 by virtue of a close frictional fit and/or the clip around the head of the medicament cartridge 19. The needle 17 is thereby inserted into the cartridge 19.

As either the retainer 53 or needle sleeve 55 is pushed further, the levers 52 bend and decouple from the retainer 53, as shown between FIGS. 6 and 7.

The force needed to bend the levers 52 must be larger than the force needed to attach the needle holder 51 to the cartridge 19 so that the decoupling of the levers 52 from the retainer 53 occurs subsequent to the attachment of the needle holder 51 to the cartridge 19.

In the embodiment shown in FIGS. 5-7, no ramp is required since the decoupling is achieved by bending the levers 52 rather than causing an outward radial movement of radial members of the retainer, as shown in FIGS. 1-4.

Further alternative embodiments provide for decoupling of the needle holder from a retainer by breaking the levers once the retainer has been pushed beyond a predetermined point. This can be done using predetermined breaking points on the lever or by pushing the lever against a sharp edge (which may be fixed to the cartridge holder) once the needle holder is attached to the medicament cartridge.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15$^{th}$ edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An example of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A medicament injection device comprising:
a main body configured to receive a medicament cartridge sealed with a penetrable barrier;
a needle holder holding a needle;
a needle sleeve arranged around at least a portion of the needle holder and needle, and arranged to be axially movable with respect to the main body; and
a retainer coupled to the needle holder and to the needle sleeve and axially movable with respect to a main body along a main axis of the device,
wherein the retainer is coupled to the needle holder so that, upon displacement of the needle sleeve and the retainer by a predefined distance towards a proximal end of the main body, the needle holder and needle are displaced axially towards the proximal end of the main body and decouple from the retainer, and
wherein the needle sleeve is configured to disengage from the needle holder upon axial displacement of the needle sleeve in a proximal direction beyond the predefined distance.

2. The device of claim 1, wherein the needle holder is configured to dock with the medicament cartridge received by the main body.

3. The device of claim 1, wherein, in a first position, the needle sleeve is coupled to the retainer so that axial movement of the needle sleeve in the proximal direction causes the axial displacement of the retainer, the needle holder, and the needle in the proximal direction.

4. The device of claim 1, wherein the needle holder comprises a female part arranged to dock with the medicament cartridge having a male part to form a frictional fit with respect to each other subsequent to displacement of the needle holder by the predefined distance.

5. The device of claim 1, wherein the needle holder further comprises a lip configured to prevent subsequent axial displacement of the needle holder and the needle with respect to the medicament cartridge subsequent to the needle holder docking with the medicament cartridge.

6. The device of claim 1, wherein the main body comprises a slotted ramp and the retainer comprises one or more radial members, wherein axial movement of the one or more radial members over the slotted ramp causes outward radial movement of the radial members, thereby causing the retainer to disengage from the needle holder.

7. The device of claim 1, wherein the needle holder comprises a flexible lever configured to flex and disengage from the retainer in response to the retainer moving axially by the predefined distance in the proximal direction.

8. The device of claim 1, wherein the retainer comprises one or more radial members each configured to separate into two parts subsequent to axial displacement by the predefined distance.

9. The device of claim 1, wherein the device contains the medicament cartridge and wherein the needle penetrates the barrier of the medicament cartridge upon displacement of the needle holder displacement member by a predefined distance in the proximal direction.

10. The device of claim 1, wherein the device contains medicament cartridge containing a medicament.

11. The device of claim 1, wherein the device is an auto-injector device.

12. A method with a medicament injection device, the medicament injection device comprising:
   a main body configured to receive a medicament cartridge sealed with a penetrable barrier;
   a needle holder holding a needle;
   a needle sleeve arranged around at least a portion of the needle holder and needle, and arranged to be axially movable with respect to the main body; and
   a retainer coupled to the needle holder and to the needle sleeve and axially movable with respect to the main body along the main axis of the device;
   wherein the retainer is coupled to the needle holder so that, upon displacement of the needle sleeve and the retainer by a predefined distance towards a proximal end of the main body, the needle holder and needle are displaced axially towards the proximal end of the main body and decouple from the retainer; and
   wherein the needle sleeve is configured to disengage from the needle holder upon axial displacement of the needle sleeve in the proximal direction beyond the predefined distance;
   the method comprising pushing the retainer in a proximal axial direction, thereby causing the needle holder and needle to be displaced axially towards the proximal end of the main body and to decouple from the retainer.

* * * * *

UNITED STATES PATENT AND TRADEMARK OFFICE
CERTIFICATE OF CORRECTION

PATENT NO. : 10,874,800 B2
APPLICATION NO. : 15/778129
DATED : December 29, 2020
INVENTOR(S) : Marc Schader et al.

It is certified that error appears in the above-identified patent and that said Letters Patent is hereby corrected as shown below:

In the Claims

Column 12, Line 35, Claim 1, delete "a" and insert -- the --

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*